(12) United States Patent
Li et al.

(10) Patent No.: US 11,933,713 B2
(45) Date of Patent: Mar. 19, 2024

(54) DETERMINING SYSTEM AND METHOD FOR WEATHERING RESISTANT CAPABILITY OF CLASTIC ROCKS IN TUNNEL BASED ON FELDSPAR FEATURES

(71) Applicant: SHANDONG UNIVERSITY, Shandong (CN)

(72) Inventors: Shucai Li, Jinan (CN); Zhenhao Xu, Jinan (CN); Ruiqi Shao, Jinan (CN); Fumin Liu, Jinan (CN); Huihui Xie, Jinan (CN); Tengfei Yu, Jinan (CN); Peng Lin, Jinan (CN); Dongdong Pan, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 322 days.

(21) Appl. No.: 17/619,203

(22) PCT Filed: Dec. 10, 2020

(86) PCT No.: PCT/CN2020/135315
§ 371 (c)(1),
(2) Date: Dec. 14, 2021

(87) PCT Pub. No.: WO2021/147554
PCT Pub. Date: Jul. 29, 2021

(65) Prior Publication Data
US 2022/0317021 A1 Oct. 6, 2022

(30) Foreign Application Priority Data
Jan. 21, 2020 (CN) .................. 2020100713131.1

(51) Int. Cl.
*G01N 17/00* (2006.01)
*G01N 1/04* (2006.01)
(Continued)

(52) U.S. Cl.
CPC .............. *G01N 17/00* (2013.01); *G01N 1/04* (2013.01); *G01N 33/24* (2013.01); *G06N 3/08* (2013.01)

(58) Field of Classification Search
CPC .......... G01N 1/04; G01N 17/00; G01N 33/24; G06N 3/08
See application file for complete search history.

(56) References Cited

U.S. PATENT DOCUMENTS

2023/0105649 A1\* 4/2023 Soua ...................... G01N 23/20
702/8

FOREIGN PATENT DOCUMENTS

CN        102053268 A     5/2011
CN        102261250 A    11/2011
(Continued)

OTHER PUBLICATIONS

ESPACENET Machine Translation of CN 109374456 A Originally Published on Feb. 22, 2022. (Year: 2022).\*

(Continued)

*Primary Examiner* — David A. Rogers
(74) *Attorney, Agent, or Firm* — Oliff PLC

(57) ABSTRACT

The present disclosure provides a determining device for the weathering resistant capability of clastic rocks in a tunnel based on feldspar features, which overcomes the shortcomings of current evaluation methods, is easy to operate, can be used to detect the type, content, and crystal structure of feldspar in a rock stratum, and integrates the information by combining a computer deep learning method to determine the weathering resistant capability of clastic rocks containing different types of feldspar in a tunnel, with high accuracy.

10 Claims, 2 Drawing Sheets

(51) Int. Cl.
*G01N 33/24* (2006.01)
*G06N 3/08* (2023.01)

(56) References Cited

FOREIGN PATENT DOCUMENTS

| CN | 102866099 | A | 1/2013 |
|---|---|---|---|
| CN | 102967548 | A | 3/2013 |
| CN | 103744109 | A | 4/2014 |
| CN | 105717149 | A | 6/2016 |
| CN | 106485223 | A | 3/2017 |
| CN | 206016814 | U | 3/2017 |
| CN | 108593531 | A | 9/2018 |
| CN | 109187161 | A | 1/2019 |
| CN | 109256179 | A | 1/2019 |
| CN | 109344516 | A | 2/2019 |
| CN | 109374456 | A | 2/2019 |
| CN | 109612943 | A | 4/2019 |
| CN | 109765097 | A | 5/2019 |
| CN | 109886329 | A | 6/2019 |
| CN | 110472597 | A | 11/2019 |
| CN | 110516730 | A | 11/2019 |
| CN | 111220616 | A | 6/2020 |
| DE | 102004063019 | A1 | 7/2006 |
| JP | H10-105546 | A | 4/1998 |
| KR | 20130133385 | A * | 12/2013 |
| WO | WO-2021043310 | A1 * | 3/2021 ............. G01T 1/202 |

OTHER PUBLICATIONS

Mar. 16, 2021 International Search Report issued in International Patent Application No. PCT/CN2020/135315.
Mar. 16, 2021 Written Opinion issued in International Patent Application No. PCT/CN2020/135315.
Sep. 17, 2020 Office Action issued in Chinese Patent Application No. 202010071313.1.
Li Riyun, "Research on Characteristic Indexes of Weathering Intensity of Rocks". Chinese Journal of Rock Mechanics and Engineering, pp. 3830-3833, Nov. 30, 2004.
Zhang, Zhongjian. "Microscopic Characteristics of Petrography and Discussion on Weathering Mechanism of Fangshan Marble in Beijing". Journal of Engineering-Geology., pp. 279-286, Dec. 31, 2015.

* cited by examiner

DETERMINING SYSTEM AND METHOD FOR WEATHERING RESISTANT CAPABILITY OF CLASTIC ROCKS IN TUNNEL BASED ON FELDSPAR FEATURES

FIELD OF THE INVENTION

The present disclosure belongs to the field of rock weathering resistance test, and relates to a determining system and method for the weathering resistant capability of clastic rocks in a tunnel based on feldspar features.

BACKGROUND OF THE INVENTION

The statement of this section merely provides background art information related to the present disclosure, and does not necessarily constitute the prior art.

Feldspar are the most common silicate minerals in the earth's crust. As the most important petrogenetic minerals in the lithosphere, their features are closely related to the structure, hardness, compressive strength, and weathering resistance of rocks. The crystallization temperature of feldspar is low, second only to quartz and muscovite, so feldspar are a class of minerals with strong weathering resistant capability. However, the traditional research for the hardness or weathering resistant capability of rocks in tunnel mostly consider quartz, but rarely consider the relationship between the weathering resistance capabilities of rocks and feldspar. However, the distribution of feldspar in the lithosphere is more extensive than quartz and other minerals. If a mineral factor that can be adapted to a variety of rocks needs to be found as much as possible, feldspar is a good choice.

Most of the minerals in clastic rocks are deposited form magmatic rocks weathered and transported. Feldspar continues to be preserved as a product of weathering, indicating that it has strong weathering resistant capability. Although a large amount of quartz also exists in clastic rocks, feldspar also has a very important impact on the weathering resistant capability of clastic rocks. However, according to the inventor's understanding, the current evaluation of the weathering resistant capability of clastic rocks in tunnels lacks consideration of feldspar features, resulting in fewer clastic rock can be studied. Meanwhile, the weathering resistance capability of rocks may be determined by means of low quartz content in tunnel, resulting in large errors.

SUMMARY

The present disclosure proposes a determining system and method for the weathering resistant capability of clastic rocks in a tunnel based on the analysis of feldspar features. The present disclosure determines the weathering resistant capability of clastic rocks in a tunnel by researching feldspar features, which fills in a gap of prediction research on the weathering resistant capability of tunnel surrounding rocks.

According to some embodiments, the present disclosure adopts the following technical solutions:

A determining system for the weathering resistant capability of clastic rocks in a tunnel based on the analysis on feldspar features, including:
  a sampling mechanism, mounted in front of a TBM (Tunnel Boring Machine) to obtain rock block or/and rock powder samples of a tunnel face;
  an automatic scanning module, configured to collect omni-directional images of a rock stratum before the samples are obtained;
  an element analysis module, configured to collect the information about chemical elements included in the samples;
  a microscopic image module, configured to extract cleavage features, interference color features, relief features and crystal structure features of feldspar in the samples;
  a wireless transmission module, configured to transmit data obtained by the automatic scanning module and the element analysis module to a data analysis center; and
  the data analysis center, configured to, according to the obtained information, obtain cleavage information and crystal structure information by extracting image features and element features, and then determine a grade of weathering resistant capability of the rock stratum.

As an alternative embodiment, the sampling mechanism includes a sampling mechanical arm and a rock breaking mechanism mounted on the TBM, the rock breaking mechanism includes a laser rock breaking device and a drilling rig, wherein the laser rock breaking system cut the block samples by laser, the drilling rig drills the powder samples, and the sampling mechanical arm is movable in multiple dimensions.

As an alternative embodiment, the automatic scanning device is equipped with a high-definition fully automatic wide-angle camera lens for collecting high-definition image information of the studied rock stratum.

As an alternative embodiment, the element analysis module includes an X-ray analysis device.

As an alternative embodiment, the system further includes a mineral quantification module, the mineral quantification module includes an electronic microprobe system, for quantitatively analyzing the content of various types of feldspar in the samples.

As an alternative embodiment, the data analysis center includes a lithology comparison module and a deep learning module, wherein the lithology comparison module receives the information obtained by the automatic scanning module, the element analysis module and the microscopic image module, and cooperates with the deep learning module.

The deep learning module is configured to extract image features and element features to feedback lithology information, compare the element content of various types of feldspar with existing data, obtain cleavage information and crystal structure information, and then perform classification to obtain the grade of weathering resistant capability of the rock stratum.

As an alternative embodiment, the deep learning module includes an artificial auxiliary neural network trainer and an automatic model predictor, the artificial auxiliary neural network trainer stores prior tunnel excavation rock data, various surface rock data, and drilling lithology data of oil and coal fields as training data to obtain the type and content of feldspar in the rocks for classifying a weathering resistant grade of a single feature and giving lithology features of the rock; the automatic model predictor is configured to carry out classification according to a weathering resistant degree classification model, and output final prediction results.

A determining method for the weathering resistant capability of clastic rocks in a tunnel based on the analysis on feldspar features including the following steps:
  collecting in advance surface clastic rock samples, oil field or coal field drilling core samples, and tunnel clastic rock in the early stage of tunnel excavation, obtaining image features, element features, microscopic features, crystal features and mineral features and the like of the samples, and completing the training of a model by using the determination criteria of different weathering grades;

randomly collecting block samples and powder samples on a tunnel face during TBM shutdown, scanning the tunnel face in omni-directions to obtain image information, and analyzing element types in the samples;

building a model through neural network learning according to the extracted images including cleavage features, interference color features, relief features and crystal structure features, repeatedly comparing with existing data to finally obtain the cleavage type, interference color features, relief features and the like and crystal structure features of feldspar for classifying a weathering resistant grade of a single feature;

quantitatively obtaining main types of minerals in the samples, combining mineral quantitative analysis results, element analysis data and image data to obtain the type and content of feldspar in rocks through the neural network pre-learning model for classifying the weathering resistant grade of the single feature, and giving lithology information of the rock; and integrating all the above information, carrying out classification through an embedded weathering resistant degree classification model, and outputting final prediction results.

As an alternative embodiment, the process of classifying a weathering resistant grade of a single feature includes: from the view of determination criteria provided for different types of feldspar, orthoclase>acid plagioclase>neutral plagioclase>basic plagioclase, the feldspar containing only K element has the strongest weathering resistant capability, the feldspar containing Na element is second, the feldspar containing only Ca element has the worst weathering resistant capability, and the weathering resistant capability of the feldspar containing both Na and Ca elements is enhanced as the content of Na element increases.

As an alternative embodiment, the process of classifying a weathering resistant grade of a single feature includes: the higher the content of feldspar in the rocks is, the stronger its weathering resistant capability is.

As an alternative embodiment, the process of classifying a weathering resistant grade of a single feature includes: the better the crystal shape of a mineral is preserved, the more stable it is, and the higher its weathering resistant capability is.

Compared with the prior art, the beneficial effects of the present disclosure are:

The present disclosure provides a method for evaluating the weathering resistant capability of clastic rocks in a tunnel by using minerals that are more widespread in the earth crust, which overcomes the shortcomings of current evaluation methods, is easy to operate, can be used to detect the type, content, and crystal structure of feldspar in a rock stratum, and integrates the information by combining a computer deep learning method to determine the weathering resistant capability of clastic rocks containing different types of feldspar in a tunnel, with high accuracy.

BRIEF DESCRIPTION OF THE DRAWINGS

The accompanying drawings constituting a part of the present disclosure are used for providing a further understanding of the present disclosure, and the schematic embodiments of the present disclosure and the descriptions thereof are used for interpreting the present disclosure, rather than constituting improper limitations to the present disclosure.

DETAILED DESCRIPTION OF EMBODIMENTS

The present disclosure will be further illustrated below in conjunction with the accompanying drawings and embodiments.

It should be noted that the following detailed descriptions are exemplary and are intended to provide further descriptions of the present disclosure. All technical and scientific terms used herein have the same meaning as commonly understood by those of ordinary skill in the technical filed to which the present disclosure belongs, unless otherwise indicated.

It should be noted that the terms used here are merely used for describing specific embodiments, but are not intended to limit the exemplary embodiments of the present disclosure. As used herein, unless otherwise clearly stated in the context, singular forms are also intended to include plural forms. In addition, it should also be understood that when the terms "comprise" and/or "include" are used in the description, it indicates the presence of features, steps, operations, devices, components, and/or combinations thereof.

Figure 1:
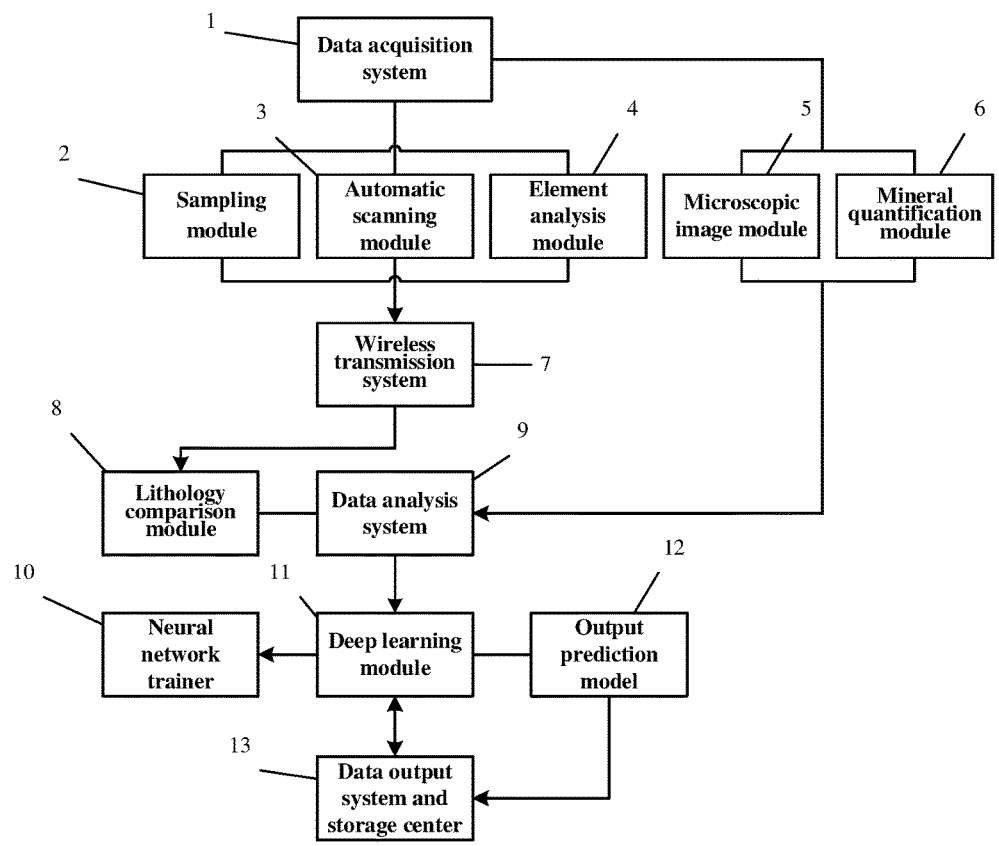
FIG. 1 is a diagram of an overall system structure of this embodiment.

As shown in FIG. 1, a determining system for the weathering resistant capability of clastic rocks in a tunnel based on the analysis on feldspar features includes a data acquisition system, a wireless transmission system, a data analysis system, and a data output and storage center, and each system further includes different modules.

Figure 2:
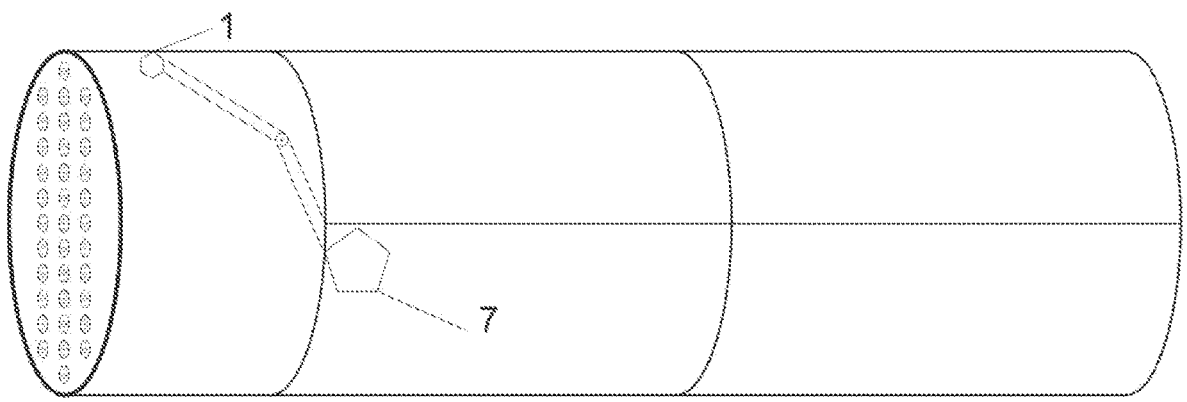
FIG. 2 is a schematic diagram of installation of a TBM data acquisition system and a wireless transmission module in a tunnel.
Figure 3:
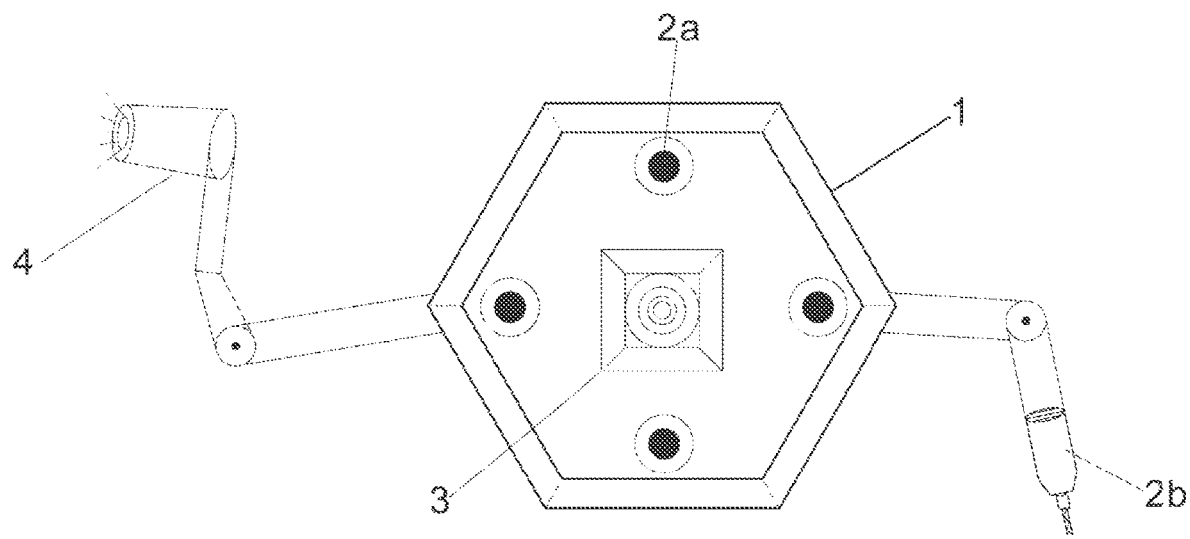
FIG. 3 is a schematic diagram of installation of a sampling mechanism and an automatic scanning module in a data acquisition system on a mechanical arm on front of a TBM.
Figure 4:
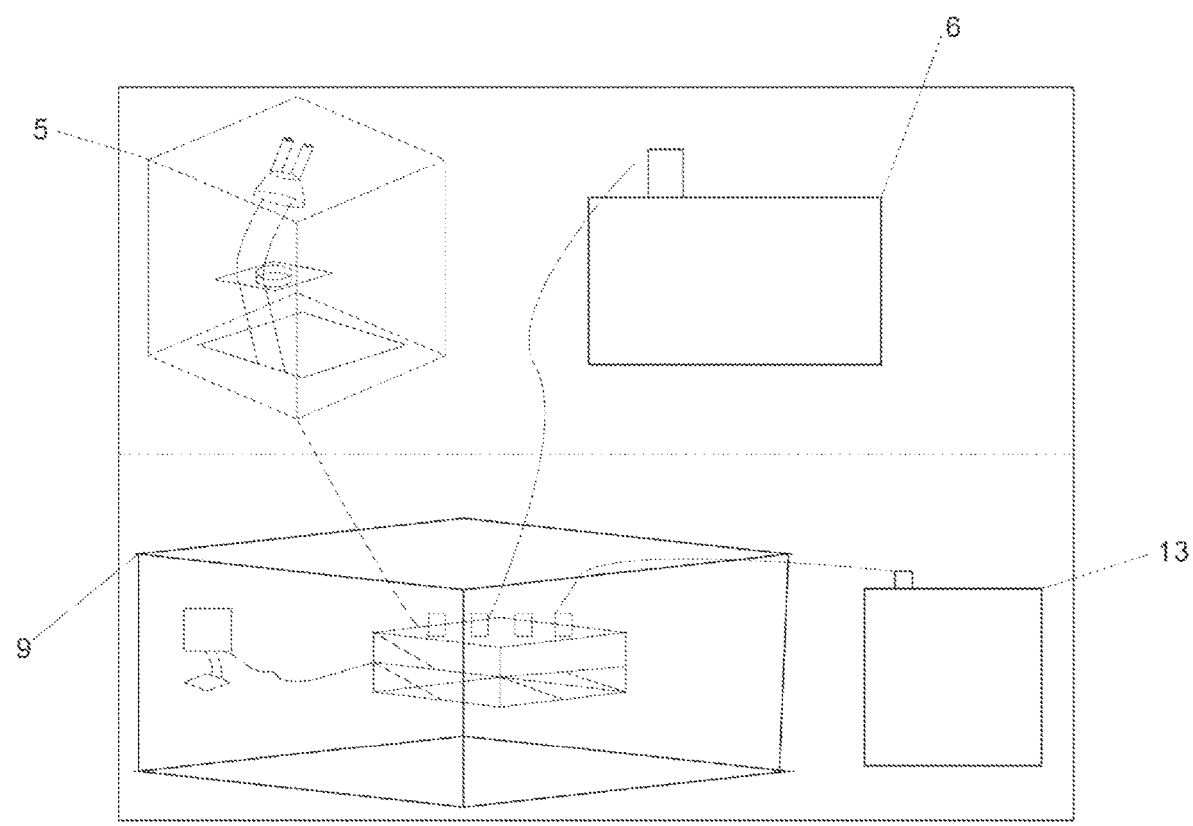
FIG. 4 is a simplified diagram of actual operation of data analysis, output and storage, display modules and a mineral quantitative analysis module.

As shown in FIGS. 2, 3 and 4, a sampling mechanism, an automatic scanning module, and an element analysis module in the data acquisition system are installed on a front end of a TBM through a mechanical arm. The sampling mechanism and the automatic scanning module can perform multi-directional random sampling and omni-directional image acquisition on a tunnel face when the TBM is shut down.

The element analysis module is equipped with an X-ray analyzer to collect information about basic chemical elements of composition the rocks.

In addition, a microscopic image module and a mineral quantification module are placed in a remote control laboratory, and the data obtained is transmitted to a deep learning module.

The microscopic image module is equipped with a high-resolution polarizing microscope, which is mainly used to extract cleavage features, interference color features, relief features and crystal structure features and transmit same to the learning module for classification.

The mineral quantification module is equipped with an electronic microprobe system. Since an X-ray system can only measure element types semi-quantitatively, the electronic microprobe system can further quantitatively analyze the content of various types of feldspar for the learning system to carry out analysis and classification.

The wireless transmission system is mounted at an end of the information acquisition system to transmit data obtained by the automatic scanning module and the element analysis module in the acquisition system to the data analysis system.

The data analysis system is placed in a remote control room, and includes a lithology comparison module and a deep learning module.

The lithology comparison module receives information from the data acquisition system, and cooperates with the deep learning module;

A lithology identification system is embedded with a lithology database, and the deep learning module can feed back the basic lithology information by extracting image features and element features.

The deep learning module includes an artificial auxiliary neural network trainer and an automatic model predictor.

The trainer has received a large amount of prior tunnel excavation rock data, various surface rock data, and drilling lithology data for oil field and coal field, these data are all stored in the data storage center, and the trainer can continuously obtain new data from the data storage center for training.

The trainer receives information from the element analysis module and the mineral quantification module, compares and trains the information with existing data, and finally can perform classification according to first and second principles.

The trainer receives microscopic image module information, performs image learning, y compares the data with the existing data in the storage center to obtain cleavage information and crystal structure information, and performs classification according to a third principle.

The trainer finally combines the three classifications to give a grade of weathering resistant capability of a rock stratum according to preset classification criteria.

The predictor compares the results to be detected with the results of various rock samples manually analyzed in the data storage center, and determines a corresponding relationship type between the weathering resistant capability and feldspar in the rocks through the model trained by the trainer as an auxiliary prediction.

The data acquisition system collects data on the tunnel face during shutdown period of the TBM, the fully automatic high-definition camera scans the tunnel face, a laser rock breaking device randomly takes block samples from the tunnel face, a small percussion drill takes powder samples, and the equipped X-ray analysis device and a corresponding data interpretation system preliminary identifies various chemical elements in the rock stratum. However, due to there are exist a large number allomerism during the development of feldspar, the electronic microprobe system is required for quantitative analysis of elemental compounds or minerals.

The microscopic image module identifies the crystal shapes (automorphic, hypautomorphic, or xenomorphism), interference colors (the interference color of orthoclase is first orde gray-gray white, and the interference color of plagioclase is first order yellow, with parallel extinction), and the reliefs (the orthoclase has low reliefs, and the plagioclase has high reliefs) based on different microscopic features of feldspar, for example, two sets of orthoclase cleavage intersect at 90°, while plagioclase cleavage does not intersect at 90°.

First principle: the feldspars type, The lower the crystallization temperature of a mineral is, the stronger its weathering resistant capability is. Different feldspars have a certain sequential order of crystallization. Therefore, the weathering resistant capability of potash feldspar is higher than that of plagioclase (that is, the orthoclase has stronger weathering resistant capability than the plagioclase), or the weathering resistant capability of alkali feldspar is greater than that of plagioclase, and the weathering resistant capability of acid plagioclase is greater than that of neutral plagioclase and greater than that of basic plagioclase. In summary, from the determination criteria provided for different types of feldspar, orthoclase (potash feldspar)>acid plagioclase (albite, oligoclase)>neutral plagioclase (andesine)>basic plagioclase (labradorite, bytownite, anorthite). By comparing the element content, the present disclosure provide a simpler classification, that is, the feldspar containing only K element has the strongest weathering resistant capability, the feldspar containing Na element is second, the feldspar containing only Ca element has the worst weathering resistant capability, and the weathering resistant capability of the feldspar containing both Na and Ca elements is enhanced as the content of Na element increases.

Second principle: the proportion of feldspar in clast of the clastic rocks. In the clastic rocks, the feldspar is originally the product of original rocks after being weathered, indicating that the feldspar itself has stronger weathering resistant capability. Therefore, the higher the content of feldspar in the clastic rocks is, the stronger its weathering resistant capability is.

Third principle: crystal structure. If the mineral has sufficient crystallization time and growth space during crystallization, it will grow into a fixed shape according to its own crystal structure. Therefore, after the mineral crystallizes, it maintains its own crystal structure and shape, which is called automorphic crystal; most of the reserved crystal is called hypautomorphiccrystal; the crystal that completely loses its shape is called xenomorphism crystal; and the better the preserved crystal shape of the mineral is, the more stable the crystal is, and the higher its weathering resistant capability is.

Based on the above principles and combined with the basic features of rocks in the lithosphere, the following determination grades are proposed: if the type of feldspar in the clastic rocks is only potash feldspar, grade 1; potash feldspar>plagioclase, grade 2; potash feldspar<plagioclase, grade 3; only plagioclase, grade 4.

If the clast content of feldspar in the clastic rocks exceeds 50%, grade 1; 15%-50%, grade 2; 5%-15%, grade 3; <5%, grade 4.

The crystal structure of feldspar, the content of automorphic>hypautomorphic+xenomorphism, grade 1; euhedral the content of automorphic+hypautomorphic>xenomorphism, grade 2; the content of automorphic≈hypautomorphic+xenomorphism, grade 3; the content of automorphic+hypautomorphic<xenomorphism, grade 4.

According to the above three criteria, the final determination grades of feldspar features on the degree of weathering of the rock stratum are provided: at least one grade 1 and grade 2 or two grades 2 indicates superior weathering resistant capability, only one grade 1 or grade 2 indicates medium weathering resistant capability, and no grade 1 or grade 2 indicates poor weathering resistant capability.

The working process of a determining system and method for the weathering resistant capability of clastic rocks in a tunnel based on the analysis on feldspar features mainly includes the following steps:
1. Surface clastic rock samples, and oil field or coal field drilling core samples, and tunnel clastic rock samples in the early stage of excavation are collected, image features, element features, microscopic features, crystal features, mineral features, etc. of the samples are obtained, and these data are imported into the data storage center (13) and the trainer (10) to provide determination criteria of different weathering grades so as to complete the training of a model;

2. During TBM shutdown, the information acquisition system (1) starts to work, the sampling module (2) randomly takes block samples (2a) and powder samples (2b) on a tunnel face, the scanning module (3) starts to carry out omni-directional scanning on the tunnel face to obtain image information, the element analysis module (4) analyzes element types in the samples, and finally, the wireless transmission system (7) transmits the data obtained in the above process to the lithology comparison module (8);

3. Meanwhile, the microscopic image module (5) transmits the extracted images including cleavage features, interference color features, relief features and crystal structure features to the data analysis system (9), the trainer (10) builds a model through neural network learning, and these data are repeatedly compared with existing data in the data storage space (13) to finally obtain the cleavage type, interference color features, relief features and crystal structure features of feldspar for classifying a weathering resistant grade of a single feature;

4. The mineral quantification module (6) can quantitatively obtain main types and content of minerals in the samples, the trainer (10) in the data analysis system (9) combines the mineral quantitative analysis results with the element analysis data from the lithology comparison module (8) and image data, the type and content of feldspar in rocks can be obtained through the neural network pre-learning model for classifying the weathering resistant grade of the single feature, and basic lithology features of the rocks can also be given;

5. After analysis through the deep learning module, the learning system integrates all the above information, carries out classification through an embedded weathering resistant degree classification model, and outputs final prediction results (12);

6. The data output system outputs the data to the storage center (13) for storage;

7. During TBM tunneling, when the system is not working, indoor standard samples and the information obtained from rock blocks excavated in the tunnel can be used for continuously learning to maximize the accuracy and reliability;

8. Steps 2 to 7 are repeated to carry out the next stage of testing and analysis.

A person skilled in the art should understand that the embodiments of the present disclosure may be provided as a method, a system, or a computer program product. Therefore, the present disclosure may be in the form of a full hardware embodiment, a full software embodiment, or an embodiment combining software and hardware. In addition, the present disclosure may be in the form of a computer program product implemented on one or more computer available storage media (including but not limited to a disk memory, a CD-ROM, an optical memory, etc.) including computer available program codes.

The present disclosure is described with reference to flowcharts and/or block diagrams of the method, device (system), and the computer program product in the embodiments of the present disclosure. It should be understood that computer program instructions can implement each process and/or block in the flowcharts and/or block diagrams and a combination of processes and/or blocks in the flowcharts and/or block diagrams. These computer program instructions may be provided to a general-purpose computer, a dedicated computer, an embedded processor, or a processor of other programmable data processing device to generate a machine, so that a device configured to implement functions specified in one or more processes in the flowcharts and/or one or more blocks in the block diagrams is generated by using instructions executed by the general-purpose computer or the processor or other programmable data processing device.

These computer program instructions can also be stored in a computer-readable memory that can guide a computer or other programmable data processing device to work in a specific manner, so that the instructions stored in the computer-readable memory generate a product including an instruction device, where the instruction device implements function specified in one or more processes in the flowcharts and/or one or more blocks in the block diagrams.

These computer program instructions can also be loaded into a computer or other programmable data processing device, so that a series of operation steps are performed on the computer or other programmable data processing device to generate processing implemented by a computer, and instructions executed on the computer or other programmable data processing device provide steps for implementing functions specified in one or more processes in the flowcharts and/or one or more blocks in the block diagrams.

Described above are merely preferred embodiments of the present disclosure, and the present disclosure is not limited thereto. Various modifications and variations may be made to the present disclosure for those skilled in the art. Any modification, equivalent substitution, improvement or the like made within the spirit and principle of the present disclosure shall fall into the protection scope of the present disclosure.

Although the specific embodiments of the present disclosure are described above in combination with the accompanying drawing, the protection scope of the present disclosure is not limited thereto. It should be understood by those skilled in the art that various modifications or variations could be made by those skilled in the art based on the technical solution of the present disclosure without any creative effort, and these modifications or variations shall fall into the protection scope of the present disclosure.

The invention claimed is:

1. A determining device for the weathering resistant capability of clastic rocks in a tunnel based on feldspar features, comprising:
    a sampling mechanism, mounted in front of a TBM to obtain rock block or/and rock powder samples of a tunnel face;
    an automatic scanning module, configured to collect omni-directional images of a rock stratum before the samples are obtained;
    an element analysis module, configured to collect the information about basic chemical elements included in the samples;
    a microscopic image module, configured to extract cleavage features, interference color features, relief features and crystal structure features of feldspar in the samples;
    a wireless transmission module, configured to transmit data obtained by the automatic scanning module and the element analysis module to a data analysis center; and
    the data analysis center, configured to, according to the obtained information, obtain cleavage information and crystal structure information by extracting image features and element features, and then determine a grade of weathering resistant capability of the rock stratum.

2. The determining device for the weathering resistant capability of clastic rocks in a tunnel based on feldspar features according to claim 1, wherein the sampling mechanism comprises a sampling mechanical arm and a rock breaking mechanism mounted on the TBM, the rock breaking mechanism comprising a laser rock breaking device and a drilling rig, wherein the laser rock breaking system cuts the block samples by laser, the drilling rig drills the powder samples, and the sampling mechanical arm is movable in multiple dimensions.

3. The determining device for the weathering resistant capability of clastic rocks in a tunnel based on feldspar features according to claim 1, wherein the automatic scanning device is equipped with a high-definition fully automatic wide-angle camera lens for collecting high-definition image information of the studied rock stratum.

4. The determining device for the weathering resistant capability of clastic rocks in a tunnel based on feldspar features according to claim 1, wherein the element analysis module includes an X-ray analysis device.

5. The determining device for the weathering resistant capability of clastic rocks in a tunnel based on feldspar features according to claim 1, further comprising a mineral quantification module, the mineral quantification module comprises an electronic microprobe system, for quantitatively analyzing the content of various types of feldspar in the samples.

6. The determining device for the weathering resistant capability of clastic rocks in a tunnel based on feldspar features according to claim 1, wherein the data analysis center comprises a lithology comparison module and a deep learning module, wherein the lithology comparison module receives the information obtained by the automatic scanning module, the element analysis module and the microscopic image module, and cooperates with the deep learning module;

the deep learning module is configured to extract image features and element features to feedback basic lithology information, compare the element content of various types of feldspar with existing data, obtain cleavage information and crystal structure information, and then perform classification to obtain the grade of weathering resistant capability of the rock stratum.

7. The determining device for the weathering resistant capability of clastic rocks in a tunnel based on feldspar features according to claim 1, wherein the deep learning module comprises an artificial auxiliary neural network trainer and an automatic model predictor, the artificial auxiliary neural network trainer stores prior tunnel excavation rock data, various surface rock data, and drilling lithology data of oil field and coal field as training data to obtain the type and content of feldspar in the rocks for classifying a weathering resistant grade of a single feature and giving basic lithology features of the rocks; the automatic model predictor is configured to carry out classification according to a weathering resistant degree classification model, and output final prediction results.

8. A determining method for the weathering resistant capability of clastic rocks in a tunnel based on feldspar features, comprising the following steps:
collecting in advance clastic rock samples, surface clastic rock samples, and oil field or coal field drilling core samples in the early stage of tunnel excavation, obtaining image features, element features, microscopic features, crystal features and mineral features and the like of the samples, and completing the training of a model by using the determination criteria of different weathering grades;
randomly collecting block samples and powder samples on a tunnel face during TBM shutdown, scanning the tunnel face in omni-directions to obtain image information, and analyzing element types in the samples;
building a model through neural network learning according to the extracted images including cleavage features, interference color features, relief features, and crystal structure features, repeatedly comparing with existing data to finally obtain the cleavage type, interference color features, relief features and the like and crystal structure features of feldspar for classifying a weathering resistant grade of a single feature;
quantitatively obtaining main types of minerals in the samples, combining mineral quantitative analysis results, element analysis data and image data to obtain the type and content of feldspar in rocks through the neural network pre-learning model for classifying the weathering resistant grade of the single feature, and giving basic lithology features of the rock; and
integrating all the above information, carrying out classification through an embedded weathering resistant degree classification model, and outputting final prediction results.

9. The determining method according to claim 8, wherein the process of classifying a weathering resistant grade of a single feature comprises: from the view of determination criteria provided for different types of feldspar, orthoclase>acid plagioclase>neutral plagioclase>basic plagioclase, the feldspar containing only K element has the strongest weathering resistant capability, the feldspar containing Na element is second, the feldspar containing only Ca element has the worst weathering resistant capability, and the weathering resistant capability of the feldspar containing both Na and Ca elements is enhanced as the content of Na element increases.

10. The determining method according to claim 8, wherein the process of classifying a weathering resistant grade of a single feature comprises: the higher the content of feldspar in the rocks is, the stronger its weathering resistant capability is;
or, the better the crystal shape of a mineral is preserved, the more stable it is, and the higher its weathering resistant capability is.

* * * * *